(12) United States Patent
Steckel et al.

(10) Patent No.: US 8,282,909 B2
(45) Date of Patent: Oct. 9, 2012

(54) PHARMACEUTICAL COMPOSITION FOR TOPICAL APPLICATION OF POORLY SOLUBLE COMPOUNDS

(75) Inventors: Hartwig Steckel, Schönkirchen (DE); Karin Hoffmann, Berlin (DE)

(73) Assignee: Intendis GmbH, Berlin (DE)

( * ) Notice: Subject to any disclaimer, the term of this patent is extended or adjusted under 35 U.S.C. 154(b) by 552 days.

(21) Appl. No.: 12/169,764

(22) Filed: Jul. 9, 2008

(65) Prior Publication Data

US 2009/0016969 A1 Jan. 15, 2009

Related U.S. Application Data (60) Provisional application No. 60/948,554, filed on Jul. 9, 2007.

(30) Foreign Application Priority Data

Jul. 9, 2007 (EP) .................... 07013369

(51) Int. Cl.
| | |
|---|---|
| *A61K 9/12* | (2006.01) |
| *A61K 47/44* | (2006.01) |
| *A61K 47/04* | (2006.01) |
| *A61K 31/4709* | (2006.01) |
| *A61K 7/00* | (2006.01) |
| *A61K 31/24* | (2006.01) |
| *C07D 405/02* | (2006.01) |

(52) U.S. Cl. .......... 424/45; 514/783; 514/770; 514/307; 514/314; 514/541; 546/148; 546/176; 424/401

(58) Field of Classification Search .................... None
See application file for complete search history.

(56) References Cited

U.S. PATENT DOCUMENTS

| | | | | |
|---|---|---|---|---|
| 5,567,420 | A * | 10/1996 | McEleney et al. | 424/60 |
| 6,235,271 | B1 * | 5/2001 | Luther et al. | 424/59 |
| 2001/0031769 | A1 * | 10/2001 | Jackman et al. | 514/340 |
| 2002/0054909 | A1 * | 5/2002 | Runkel | 424/484 |
| 2003/0118621 | A1 * | 6/2003 | Heidenfelder et al. | 424/401 |
| 2004/0052746 | A1 * | 3/2004 | Tamareselvy et al. | 424/70.11 |
| 2004/0228824 | A1 * | 11/2004 | Voigt et al. | 424/70.16 |
| 2004/0265249 | A1 * | 12/2004 | Arquette | 424/59 |
| 2006/0116396 | A1 * | 6/2006 | Jaroch et al. | 514/307 |

* cited by examiner

*Primary Examiner* — Brian-Yong S Kwon
*Assistant Examiner* — Hong Yu
(74) *Attorney, Agent, or Firm* — Millen, White, Zelano & Branigan, PC (57) ABSTRACT

The present invention provides a formulation which contains a poorly water soluble pharmaceutically active compound at a concentration of 50 mg per 100 g formulation or above. The solubility is achieved by a mixture of solvents as described herein. Moreover the formulation as described herein may be used as a base formulation to generate a cream, an ointment, a spray, a foam or an oleogel.

33 Claims, 1 Drawing Sheet

Fig. 1

Fig. 2

PHARMACEUTICAL COMPOSITION FOR TOPICAL APPLICATION OF POORLY SOLUBLE COMPOUNDS

This application claims the benefit of the filing date of U.S. Provisional Application Ser. No. 60/948,554 filed Jul. 9, 2007.

BACKGROUND OF THE INVENTION

Topically administered active substances are mainly used to treat the redness, swelling, itching and discomfort of psoriasis, atopic dermatitis and other pathologies of the skin. The majority of such active drug substances exhibit poor solubility in standard solvents, such as water. Poor solubility in the context of this application means that the solubility of the compound in water is 20 mg/l or less at 20° C. Glucocorticosteroids, steroids, calcineurin inhibitors, vitamin D analoques, retinoids, immunosuppressants, antimycotics, antiinfectives, estrogens, androgens, fumaric acid esters are typical drug classes for topical administration with such low water solubility. Other examples for such poorly soluble compounds are provided e.g. in WO 03/082827 or WO 2006/050998. One example is the non-steroidal active substance having the chemical name (R)-1,1,1-Trifluoro-4-(5-fluoro-2,3-dihydrobenzofuran-7-yl)-4-methyl-2-{[(2-methyl-5-quinolyl)amino]methyl}pentan-2-ol, the empirical formula of which is $C_{25}H_{26}F_4N_2O_2$, having a molecular weight of 462.5. This is the compound according to example 1 of WO 2006/050998 (hereinafter Ex1/998). Said compound is a crystalline, non-polymorphic yellowish-to-green powder that is insoluble in water, only slightly soluble in hexane and moderately soluble in ethyl alcohol. It has very poor solubility in standard cream and ointment vehicles being in use for the topical administration, such as petrolatum and mineral oils.

Commercially, topically administered drug products are available as solutions, suspensions, creams and ointments. U.S. Pat. No. 3,892,856 describes the use of corticosteroids dissolved in polyethylene glycol and emulsified into an oleaginous base. Another option to present poorly water-soluble compounds for patient use is the formulation of an oil-in-water type formulation containing the active compound in suspended form.

Other examples can be found in the scientific and patent literature.

It was the object of the present invention to provide a formulation containing the drug substance at a concentration of at least 0.1% in dissolved state in order to achieve an increased in vitro release rate and a higher efficacy in vivo.

GENERAL DESCRIPTION OF THE INVENTION

The present invention provides a formulation which contains a poorly water soluble pharmaceutically active compound at a concentration of 50 mg per 100 g formulation or above. The solubility is achieved by a mixture of solvents as described below. Moreover the formulation as described below as well as in claim 1 may be used as a base formulation to generate a cream, an ointment, a spray, a foam or an oleogel.

The base formulation contains oleyl alcohol, cetearyl octanoate and a vegetable oil in addition to one or more poorly soluble pharmaceutical compounds.

One embodiment of the invention is therefore a pharmaceutical formulation (base formulation) containing at least one pharmaceutically active compound as well as a) oleyl alcohol,
b) cetearyl octanoate and
c) a vegetable oil.

In a preferred embodiment the solubility of at least one of the pharmaceutically active compounds in water is 20 mg/l or less at 20° C. In an even more preferred embodiment the solubility of at least one of the pharmaceutically active compounds in water is 2 mg/l or less at 20° C., or even 1 mg/l or less at 20° C.

Examples for such compounds include
  glucocorticosteroids, steroids, calcineurin inhibitors, vitamin D analoques, retinoids, immunosuppressants, antimycotics, antiinfectives, estrogens, androgens, fumaric acid esters
  glucocorticoids, including but not limited to betametasone, clobetasol, dexametasone, prednicarbate, clocortolone, mometasone, methylprednisolone, esters and salts thereof
  antimycotic drug substances, including but not limited to bifonazole, clotrimazole, itraconazole, fluconazole, terbinafine
  a vitamin D analogue, including but not limited to Calcipotriol, Calcitriol, Tacalcitol
  (R)-1,1,1-Trifluoro-4-(5-fluoro-2,3-dihydrobenzofuran-7-yl)-4-methyl-2-{[(2-methyl-5-quinolyl)amino]methyl}pentan-2-ol (Ex1/998) or other compounds disclosed in WO 2006/050998 or WO 03/082827, such as the compounds selected from:
    5-[4-(5-Fluoro-2,3-dihydrobenzofuran-7-yl)-2-hydroxy-4-methyl-2-trifluoromethyl-pentylamino]-2-methylquinoline,
    5-[4-(5-Fluoro-2,3-dihydrobenzofuran-7-yl)-2-hydroxy-4-methyl-2-trifluoromethyl-pentylamino]-1-methylisoquinoline),
    5-[4-(5-Fluoro-2,3-dihydrobenzofuran-7-yl)-2-hydroxy-4-methyl-2-trifluoromethyl-pentylamino]isoquinol-1(2H)-one,
    5-[4-(5-Fluoro-2,3-dihydrobenzofuran-7-yl)-2-hydroxy-4-methyl-2-trifluoromethyl-pentylamino]-2,6-dimethylquinoline,
    5-[4-(5-Fluoro-2,3-dihydrobenzofuran-7-yl)-2-hydroxy-4-methyl-2-trifluoromethyl-pentylamino]-6-chloro-2-methylquinoline,
    5-[4-(5-Fluoro-2,3-dihydrobenzofuran-7-yl)-2-hydroxy-4-methyl-2-trifluoromethyl-pentylamino]isoquinoline,
    5-[4-(5-Fluoro-2,3-dihydrobenzofuran-7-yl)-2-hydroxy-4-methyl-2-trifluoromethyl-pentylamino]quinoline,
    5-[4-(2,3-Dihydro-5-fluoro-7-benzofuranyl)-2-hydroxy-4-methyl-2-trifluoromethyl-pentylamino]quinolin-2[1H]-one,
    6-Fluoro-5-[4-(5-fluoro-2,3-dihydrobenzofuran-7-yl)-2-hydroxy-4-methyl-2-trifluoromethyl-pentylamino]-2-methylquinoline,
    8-Fluoro-5-[4-(5-fluoro-2,3-dihydrobenzofuran-7-yl)-2-hydroxy-4-methyl-2-trifluoromethyl-pentylamino]-2-methylquinoline,
    5-[4-(5-Fluoro-2,3-dihydrobenzofuran-7-yl)-2-hydroxy-4-methyl-2-trifluoromethyl-pentylamino]-2-methylisoquinol-1(2H)-one, as well as their separate enantiomers:
    2(R)-5-[4-(5-Fluoro-2,3-dihydrobenzofuran-7-yl)-2-hydroxy-4-methyl-2-trifluoromethyl-pentylamino]-2-methylquinoline), 2(R)-5-[4-(5-fluoro-2,3-dihydrobenzofuran-7-yl)-2-hydroxy-4-methyl-2-trifluoromethyl-pentylamino]-1-methylisoquinoline, 2(R)-5-[4-(5-Fluoro-2,3-dihydrobenzofuran-7-yl)-2-hydroxy-4-methyl-2-trifluoromethyl-pentylamino]isoquinol-1(2H)-one, 2(R)-5-[4-(5-Fluoro-2,3-dihydrobenzofuran-7-yl)-2-hydroxy-4-methyl-2-trifluoromethyl-pentylamino]-2,6-dimethylquinoline, 2(R)-5-[4-(5-Fluoro-2,3-dihydrobenzofuran-7-yl)-2-hydroxy-4-methyl-2-trifluoromethyl-pentylamino]-6-chloro-2-methylquinoline, 2(R)-5-[4-(5-Fluoro-2,3-dihydrobenzofuran-7-yl)-2-hydroxy-4-methyl-2-trifluoromethyl-pentylamino]isoquinoline, 2(R)-5-[4-(5-Fluoro-2,3-dihydrobenzofuran-7-yl)-2-hydroxy-4-methyl-2-trifluoromethyl-pentylamino]quinoline, 2(R)-5-[4-(2,3-Dihydro-5-fluoro-7-benzofuranyl)-2-hydroxy-4-methyl-2-trifluoromethyl-pentylamino]quinolin-2[1H]-one, 2(R)-6-Fluoro-5-[4-(5-fluoro-2,3-dihydrobenzofuran-7-yl)-2-hydroxy-4-methyl-2-trifluoromethyl-pentylamino]-2-methylquinoline, 2(R)-8-Fluoro-5-[4-(5-fluoro-2,3-dihydrobenzofuran-7-yl)-2-hydroxy-4-methyl-2-trifluoromethyl-pentylamino]-2-methylquinoline, 2(R)-5-[4-(5-Fluoro-2,3-dihydrobenzofuran-7-yl)-2-hydroxy-4-methyl-2-trifluoromethyl-pentylamino]-2-methylquinol-1(2H)-one, 2(S)-5-[4-(5-Fluoro-2,3-dihydrobenzofuran-7-yl)-2-hydroxy-4-methyl-2-trifluoromethyl-pentylamino]-2-methylquinoline), 2(S)-5-[4-(5-Fluoro-2,3-dihydrobenzofuran-7-yl)-2-hydroxy-4-methyl-2-trifluoromethyl-pentylamino]-1-methylisoquinoline), 2(S)-5-[4-(5-Fluoro-2,3-dihydrobenzofuran-7-yl)-2-hydroxy-4-methyl-2-trifluoromethyl-pentylamino]isoquinol-1(2H)-one, 2(S)-5-[4-(5-Fluoro-2,3-dihydrobenzofuran-7-yl)-2-hydroxy-4-methyl-2-trifluoromethyl-pentylamino]-2,6-dimethylquinoline, 2(S)-5-[4-(5-Fluoro-2,3-dihydrobenzofuran-7-yl)-2-hydroxy-4-methyl-2-trifluoromethyl-pentylamino]-6-chloro-2-methylquinoline, 2(S)-5-[4-(5-Fluoro-2,3-dihydrobenzofuran-7-yl)-2-hydroxy-4-methyl-2-trifluoromethyl-pentylamino]isoquinoline, 2(S)-5-[4-(5-Fluoro-2,3-dihydrobenzofuran-7-yl)-2-hydroxy-4-methyl-2-trifluoromethyl-pentylamino]quinoline, 2(S)-5-[4-(2,3-Dihydro-5-fluoro-7-benzofuranyl)-2-hydroxy-4-methyl-2-trifluoromethyl-pentylamino]quinolin-2[1H]-one, 2(S)-6-Fluoro-5-[4-(5-fluoro-2,3-dihydrobenzofuran-7-yl)-2-hydroxy-4-methyl-2-trifluoromethyl-pentylamino]-2-methylquinoline, 2(S)-8-Fluoro-5-[4-(5-fluoro-2,3-dihydrobenzofuran-7-yl)-2-hydroxy-4-methyl-2-trifluoromethyl-pentylamino]-2-methylquinoline, 2(S)-5-[4-(5-Fluoro-2,3-dihydrobenzofuran-7-yl)-2-hydroxy-4-methyl-2-trifluoromethyl-pentylamino]-2-methylisoquinol-1(2H)-one 1-(Quinolin-8-ylamino)-4-(5-fluoro-2-methoxyphenyl)-4-methyl-2-(trifluoromethyl)pentan-2-ol 1-(Quinolin-8-ylamino)-4-(5-fluoro-2-hydroxyphenyl)-4-methyl-2-(trifluoromethyl)pentan-2-ol 1-(Quinolin-5-ylamino)-4-(5-fluoro-2-methoxyphenyl)-4-methyl-2-(trifluoromethyl)pentan-2-ol 1-(Quinolin-5-ylamino)-4-(5-fluoro-2-methoxyphenyl)-4-methyl-2-(trifluoromethyl)pentan-2-ol 1-(Quinolin-4-ylamino)-4-(5-fluoro-2-methoxyphenyl)-4-methyl-2-(trifluoromethyl)pentan-2-ol 1-(Quinolin-4-ylamino)-4-(5-fluoro-2-hydroxyphenyl)-4-methyl-2-(trifluoromethyl)pentan-2-ol 4-(5-Fluoro-2-methoxyphenyl)-1-(isoquinolin-1-ylamino)-4-methyl-2-(trifluoromethyl)pentan-2-ol 4-(5-Fluoro-2-hydroxyphenyl)-1-(isoquinolin-1-ylamino)-4-methyl-2-(trifluoromethyl)pentan-2-ol 1-(Quinolin-5-ylamino)-4-methyl-4-phenyl-2-(trifluoromethyl)pentan-2-ol 1-(Quinolin-5-ylamino)-4-methyl-4-phenyl-2-(trifluoromethyl)pentan-2-ol 4-Methyl-1-(2-methylquinolin-5-ylamino)-4-phenyl-2-(trifluoromethyl)pentan-2-ol N-(Quinolin-5-yl)-4-(5-fluoro-2-methoxyphenyl)-2-hydroxy-4-methyl-2-(trifluoromethyl)pentanoic Acid Amide 4-(1,3-Benzodioxol-4-yl)-N-(quinolin-5-yl)-2-hydroxy-4-methyl-2-(trifluoromethyl)pentanamide N-(Quinolin-5-yl)-4-(2-chlorophenyl)-2-hydroxy-4-methyl-2-(trifluoromethyl-)-pentanamide N-(Quinolin-5-yl)-4-(2-chloro-5-fluorophenyl)-2-hydroxy-4-methyl-2-(trifluoromethyl)pentanamide N-(Quinolin-5-yl)-3-[1-(2-chloro-4-fluorophenyl)-cyclopropyl]-2-hydroxy-2-(trifluoromethyl)propanamide 4-(4-Bromo-2-methoxyphenyl)-1-(quinolin-5-ylamino)-2-hydroxy-4-methyl-2-(trifluoromethyl)pentan-2-ol 4-(5-Bromo-2-methoxyphenyl)-N-(quinolin-5-yl)-2-hydroxy-4-methyl-2-(trifluoromethyl)pentanamide 4-(4-Bromo-2-methoxyphenyl)-N-(quinolin-5-yl)-2-hydroxy-4-methyl-2-(trifluoromethyl)pentanamide N-(Quinolin-5-yl)-)-2-hydroxy-4-methyl-4-phenyl-2-(trifluoromethyl)pentanamide 4-(5-Fluoro-2-methoxyphenyl)-1-(2-methoxyquinolin-5-ylamino)-4-methyl-2-(trifluoromethyl)pentan-2-ol 4-(5-Fluoro-2-hydroxyphenyl)-1-(2-methoxyquinolin-5-ylamino)-4-methyl-2-(trifluoromethyl)pentan-2-ol 1-(2-Ethoxyquinolin-5-ylamino)-4-(5-fluoro-2-methoxyphenyl)-4-methyl-2-(trifluoromethyl)pentan-2-ol 4-(5-Fluoro-2-methoxyphenyl)-1-(2-hydroxyquinolin-5-ylamino)-4-methyl-2-(trifluoromethyl)pentan-2-ol 4-(5-Fluoro-2-methoxyphenyl)-1-(2-quinolon-5-ylamino)-4-methyl-2-(trifluoromethyl)pentan-2-ol 1-(2-Acetylaminoquinolin-5-ylamino)-4-(5-fluoro-2-hydroxyphenyl)-4-methyl-2-(trifluoromethyl)pentan-2-ol 4-(5-Fluoro-2-hydroxyphenyl)-4-methyl-1-(2-(methylamino)quinolin-5-ylamino-)-2-(trifluoromethyl)pentan-2-ol 4-(5-Fluoro-2-methoxyphenyl)-4-methyl-1-(2-methylquinolin-5-ylamino)-2-(trifluoromethyl)pentan-2-ol 4-(5-Fluoro-2-hydroxyphenyl)-4-methyl-1-(2-methylquinolin-5-ylamino)-2-(trifluoromethyl)-pentan-2-ol 5-[4-(5-Fluoro-2-methoxyphenyl)-2-hydroxy-4-methyl-2-trifluoromethylpentylamino]quinoline-2-carboxylic Acid Amide 5-[4-(5-Fluoro-2-methoxyphenyl)-2-hydroxy-4-methyl-2-trifluoromethylpentylamino]quinoline-2-carboxylic Acid Amide 5-[4-(5-Fluoro-2-hydroxyphenyl]-2-hydroxy-4-methyl-2-trifluoromethylpentylamino]quinoline-2-carboxylic Acid Amide 4-(5-Fluoro-2-methoxyphenyl)-4-methyl-2-trifluoromethyl-1-(2-(trifluoromethyl)quinolin-5-ylamino)pentan-2-ol 4-(5-Fluoro-2-hydroxyphenyl)-4-methyl-2-trifluoromethyl-1-(2-(trifluoromethyl)quinolin-5-ylamino)pentan-2-ol 1-(2-(Acetoxymethyl)quinolin-5-ylamino)-4-(5-fluoro-2-methoxyphenyl)-4-methyl-2-(trifluoromethyl)pentan-2-ol 4-(5-Fluoro-2-methoxyphenyl)-1-(2-(hydroxymethyl)quinolin-5-ylamino)-4-methyl-2-(trifluoromethyl)pentan-2-ol 4-(5-Fluoro-2-hydroxyphenyl)-1-(2-(hydroxymethyl)quinolin-5-ylamino)-4-methyl-2-(trifluoromethyl)pentan-2-ol 5-[4-(5-Fluoro-2-hydroxyphenyl)-2-hydroxy-4-methyl-2-(trifluoromethyl)pentylamino]-quinoline-2-carboxylic Acid Methylamide 3-[1-(5-Fluoro-2-hydroxyphenyl)cycloprop-1-yl]-1-(2-(hydroxymethyl)quinolin-5-ylamino)-2-(trifluoromethyl)propan-2-ol 5-[(4-(5-Fluoro-2-methoxyphenyl)-2-hydroxy-4-methyl-2-(trifluoromethyl)pentylamino]quinoline-2-carboxylic Acid Diethylamide corticosteroids, such as prednisone or fludrocortisone, calcineurin inhibitors, such as tacrolimus or pimecrolimus.

In a further embodiment of the invention the base formulation contains 2 to 50% (by weight) of oleyl alcohol, preferably 5 to 20%.

In another embodiment of the invention the base formulation contains 2 to 50% (by weight) of cetearyl octanoate, preferably 5 to 20%.

In a still further embodiment of the invention the base formulation contains 2 to 50% (by weight) of vegetable oil, preferably 5 to 20%.

Examples of such vegetable oils but not limited to these are soybean oil, olive oil, sesame oil, or peanut oil. It has to be understood that the vegetable oil may be a mixture of different vegetable oils. Preferably the vegetable oil is soybean oil.

Oil-in-Water Cream Formulation

The base formulation described above may be formulated into an oil-in-water cream. Such cream formulation is characterized in that it may contain a high content of aqueous phase (the non-solvent phase) of about 60%, in which stabilization of said two phase system is obtained by using polymeric stabilizers rather than surfactants. The latter is worth mentioning as surfactants typically exert an irritating effect on skin while the formulation described here omits the use of high amounts of surfactants.

In summary, it is possible according to the present invention to formulate poorly water-soluble drug substances as described above in a novel oil-in-water cream vehicle containing a specifically designed mixture of oily components that retain the active drug substance in a dissolved state during manufacture and for the shelf-life of the drug product.

Surprisingly, and in contrast to what could be expected, the oil-in-water cream formulation described here shows an obviously higher drug release rate and better in-vivo efficacy than observed for a fatty ointment composition which is normally used to achieve a high dermal penetration of the drug substance as a result of the occlusivity of such a vehicle. These results are particularly surprising because the tailor-made fatty ointment additionally contains a high concentration of penetration enhancers, which normally causes another additive effect on the in-vitro release rate and in-vivo efficacy.

The oil-in-water cream is stable, produces an effective biological activity and was found to be non-irritating to the skin when applied.

One further embodiment of the invention is therefore a pharmaceutical formulation in form of a oil-in-water cream formulation containing at least one pharmaceutically active compound as well as
 a) oleyl alcohol,
 b) cetearyl octanoate and
 c) a vegetable oil
 d) propylene glycol
 e) glycerol.

In a preferred embodiment the solubility of at least one of the pharmaceutically active compounds in water is 20 mg/l or less at 20° C.

In a further embodiment of the invention the oil-in-water cream formulation contains 3 to 15% (by weight) of oleyl alcohol, preferably 5 to 10%.

In another embodiment of the invention the oil-in-water cream formulation contains 2 to 15% (by weight) of cetearyl octanoate, preferably 3 to 10%.

In a still further embodiment of the invention the oil-in-water cream formulation contains 3 to 15% (by weight) of vegetable oil, preferably 4 to 6%.

In a still further embodiment of the invention the oil-in-water cream formulation contains 4 to 10% (by weight) of glycerol (85%), preferably approximately 8%.

In a still further embodiment of the invention the oil-in-water cream formulation contains 4 to 10% (by weight) of propylene glycol, preferably approximately 8%.

Examples of such vegetable oils include soybean oil, olive oil, sesame oil, castor oil or peanut oil. It has to be understood that the vegetable oil may be a mixture of different vegetable oils. Preferably the vegetable oil is soybean oil.

Cream formulations according to the present invention may furthermore contain medium-chained triglycerides, mineral oils, cyclomethicone, stearyl alcohol, butylated hydroxytoluene, macrogolglycerolhydroxystearate, povidone, acrylic acid copolymer, hydroxyethylcellulose, acrylic acid, trometamol, or mixtures thereof.

Additional unique aspects of the above described O/W cream formulation are:
 it is formulated without the use of classical emulsifiers and mainly polymer-stabilized.
 the composition of the water-phase (propylene glycol and glycerol) allows for omission of preservatives.

Oleogel Formulation

The base formulation described in the beginning may also be turned into an oleogel formulation. Such oleogel formulation is characterized in that it is a gelated viscous formulation of the described lipid blend as herein described.

One further embodiment of the invention is therefore a pharmaceutical formulation in form of an oleogel formulation containing at least one pharmaceutically active compound as well as
 a) oleyl alcohol,
 b) cetearyl octanoate and
 c) a vegetable oil
 d) silicon dioxide or aluminium stearate.

In a preferred embodiment the solubility of at least one of the pharmaceutically active compounds in water is 20 mg/l or less at 20° C.

In a further embodiment of the invention the oleogel formulation contains 10 to 40% (by weight) of oleyl alcohol, preferably 15 to 30%.

In another embodiment of the invention the oleogel formulation contains 5 to 40% (by weight) of cetearyl octanoate, preferably 10 to 30%.

In a still further embodiment of the invention the oleogel formulation contains 10 to 30% (by weight) of vegetable oil, preferably 15 to 20%.

In yet another embodiment of the invention the oleogel formulation contains 3 to 10% (by weight) of silicone dioxide, preferably 4 to 5%, or 2 to 8% (by weight) of aluminium stearate, preferably 3 to 6%.

Examples of such vegetable oils include soybean oil, olive oil, sesame oil, castor oil or peanut oil. It has to be understood that the vegetable oil may be a mixture of different vegetable oils. Preferably the vegetable oil is soybean oil.

Oleogel formulations according to the present invention may furthermore contain medium-chained triglycerides, mineral oils, cyclomethicone, or mixtures thereof.

Spray Formulation

The base formulation described in the beginning may also be turned into a spray formulation. Such spray formulation is characterized in that it contains the pharmaceutically active compound in dissolved state and is stored in a container from which it may be sprayed to the skin of a patient.

One further embodiment of the invention is therefore a pharmaceutical formulation in form of a spray formulation containing at least one pharmaceutically active compound as well as
- a) oleyl alcohol,
- b) cetearyl octanoate,
- c) a vegetable oil and
- d) mineral oil.

In a preferred embodiment the solubility of at least one of the pharmaceutically active compounds in water is 20 mg/l or less at 20° C.

In a further embodiment of the invention the spray formulation contains 10 to 50% (by weight) of oleyl alcohol, preferably 10 to 40%.

In another embodiment of the invention the spray formulation contains 10 to 50% (by weight) of cetearyl octanoate, preferably 20 to 40%.

In a still further embodiment of the invention the spray formulation contains 10 to 50% (by weight) of vegetable oil, preferably 16 to 30%.

In yet another embodiment of the invention the spray formulation contains 2 to 15% (by weight) of mineral oil, preferably 4 to 15%.

Examples of vegetable oils include soybean oil, olive oil, sesame oil, castor oil or peanut oil. It has to be understood that the vegetable oil may be a mixture of different vegetable oils. Preferably the vegetable oil is soybean oil.

Spray formulations may furthermore contain medium-chained triglycerides, cyclomethicone, or mixtures thereof.

Foam Formulation

The base formulation described in the beginning may also be turned into a foam formulation. Such foam formulation is characterized in that it contains the pharmaceutically active compound in dissolved state and is contained in a pressurized can from which the foam is created upon release by evaporation of the propellant.

One further embodiment of the invention is therefore a pharmaceutical formulation in form of a foam formulation containing at least one pharmaceutically active compound as well as
- a) oleyl alcohol,
- b) cetearyl octanoate and
- c) a vegetable oil
- d) propylene glycol
- e) glycerol
- f) a propellant.

In a preferred embodiment the solubility of at least one of the pharmaceutically active compounds in water is 20 mg/l or less at 20° C.

In a further embodiment of the invention the lipid phase of the foam formulation contains 2 to 15% (by weight) of oleyl alcohol, preferably 3 to 10%.

In another embodiment of the invention the lipid phase of the foam formulation contains 2 to 10% (by weight) of cetearyl octanoate, preferably 3 to 5%.

In a still further embodiment of the invention the lipid phase of the foam formulation contains 2 to 10% (by weight) of vegetable oil, preferably 3 to 5%.

In yet another embodiment of the invention the foam formulation contains 2 to 10% (by weight) of glycerol (85%), preferably 4 to 8%.

In a still further embodiment of the invention the foam formulation contains 2 to 10% (by weight) of propylene glycol, preferably 4 to 10%.

In another embodiment of the invention the foam formulation contains 2 to 10% (by weight) of propellant, preferably 6 to 8%.

Propellants are compounds that are gases under atmospheric pressure at room temperature but that may by liquefied at room temperature by pressurization. Examples of propellants include hydrocarbons such as propane, butane, isobutane or a mixture of these; a hydrofluoroalkane such as heptafluoropropane or tetrafluoroethane as well as dimethylether, or mixtures thereof.

Examples of vegetable oils include soybean oil, olive oil, sesame oil, castor oil or peanut oil. It has to be understood that the vegetable oil may be a mixture of different vegetable oils. Preferably the vegetable oil is soybean oil.

Foam formulations may furthermore contain macrogolglycerolhydroxystearate, macrogol-400-stearate, methylcellulose, xanthan gum or mixtures thereof.

DEFINITIONS

1. Alternative hydrophilic polymers: acrylic acid copolymer, acrylic acid, cellulose ethers, such as hydroxyethylmethylcellulose, hydroxyethylcellulose and methylcellulose, polyvinylalcohol, polyvinylpyrollidone, xanthan gum, alginates, chitosan.

2. An oily spray by definition of the invention should be understood as a liquid, sprayable formulation containing the active drug in dissolved state and is composed of the core formulation containing at least a vegetable oil, oleyl alcohol and cetearyloctanoate.

3. An oleogel by definition of the invention should be understood as a gelated, viscous formulation containing the active drug in dissolved state and is composed of the core formulation containing at least a vegetable oil, oleyl alcohol and cetearyloctanoate where the gelling is obtained by addition of a thickening agent, such as e.g. silicon dioxide and/or aluminium stearate.

4. A foam by definition of the invention should be understood as formulation containing the active drug in dissolved state and is composed of the core formulation containing at least a vegetable oil, oleyl alcohol and cetearyloctanoate, and an aqueous phase composed as in the examples. The foam is created upon release from a pressurized can and by evaporation of the liquefied propellant (the liquefied propellant being a hydrocarbon propellant such as propane, butane, isobutane or a mixture of these; a hydrofluoroalkane such as heptafluoropropane or tetrafluoroethane; dimethylether or mixtures of these)

Manufacture of the Formulations:

The formulations according to the present invention may be manufactured according to the methods well-known to the expert in the art. Such manufacturing technologies are also well described in the literature, as 'Pharmaceutical Emulsions and Suspensions' by Francoise Nielloud & Gilberte Marti-Mestres, Marcel Dekker, New York and 'Food Emulsions'—Food Science and Technology, by Stig Friberg, Kare Larsson & Stig E. Friberg, Marcel Dekker, New York.

The basic steps for the manufacture are summarized below.

O/W Cream:
1. Melting of the fat components; Dissolution of active drug substance
2. Preparation of water phase
3. Combination of water and fat phase
4. Homogenization
5. Filling Foam:
1. Melting of the fat components; Dissolution of active drug substance
2. Preparation of water phase
3. Combination of water and fat phase
4. Homogenization
5. Filling into aluminium cans
6. Valve crimping
7. Filling of propellant Spray:
1. Mixing of fat components; Dissolution of active drug substance
2. Filling Oleogel:
1. Melting of the fat components; Dissolution of active drug substance
2. Addition of gelling agent
3. Filling

OBJECTS OF THE INVENTION

The following items are therefore objects of the invention:
1. Pharmaceutical formulation containing at least one pharmaceutically active compound as well as
   a) oleyl alcohol,
   b) cetearyl octanoate and
   c) a vegetable oil.
2. Pharmaceutical formulation according to item 1, characterized in that the formulation contains 2 to 50% (by weight) of oleyl alcohol, preferably 5 to 20%
3. Pharmaceutical formulation according to at least one of the preceding items, characterized in that the formulation contains 2 to 50% (by weight) of cetearyl octanoate, preferably 3 to 20%.
4. Pharmaceutical formulation according to at least one of the preceding items, characterized in that the formulation 2 to 50% (by weight) of vegetable oil, preferably 5 to 20%.
5. Pharmaceutical formulation according to at least one of the preceding items, characterized in that the vegetable oil is soybean oil, olive oil, sesame oil, castor oil or peanut oil.
6. Pharmaceutical formulation according to item 1 furthermore containing
   d) propylene glycol
   e) glycerol.
7. Pharmaceutical formulation according to item 6, characterized in that the formulation contains 3 to 15% (by weight) of oleyl alcohol, preferably 5 to 10%.
8. Pharmaceutical formulation according to item 6, characterized in that the formulation contains 2 to 15% (by weight) of cetearyl octanoate, preferably 3 to 10%.
9. Pharmaceutical formulation according to item 6, characterized in that the formulation contains 3 to 15% (by weight) of vegetable oil, preferably 4 to 6%.
10. Pharmaceutical formulation according to item 6, characterized in that the formulation contains 4 to 10% (by weight) of glycerol (85%), preferably 8%.
11. Pharmaceutical formulation according to item 6, characterized in that the formulation 4 to 10% (by weight) of propylene glycol, preferably 8%.
12. Pharmaceutical formulation according to at least one of items 6-11, characterized in that the formulation contains furthermore medium-chained triglycerides, mineral oil, cyclomethicone, stearyl alcohol, butylated hydroxytoluene, macrogolglycerolhydroxystearate, povidone, acrylic acid copolymer, hydroxyethylcellulose, acrylic acid, trometamol.
13. Pharmaceutical formulation according to item 1 furthermore containing
   d) silicon dioxide.
14. Pharmaceutical formulation according to item 1 furthermore containing
   d) aluminium stearate.
15. Pharmaceutical formulation according to item 13 and 14, characterized in that the formulation contains 10 to 40% (by weight) of oleyl alcohol, preferably 15 to 30%.
16. Pharmaceutical formulation according to item 13 and 14, characterized in that the formulation contains 5 to 40% (by weight) of cetearyl octanoate, preferably 10 to 30%.
17. Pharmaceutical formulation according to item 13 and 14, characterized in that the formulation contains 10 to 30% (by weight) of vegetable oil, preferably 15 to 20%.
18. Pharmaceutical formulation according to item 14, characterized in that the formulation contains 3 to 10% (by weight) of silicone dioxide, preferably 4 to 5%.
19. Pharmaceutical formulation according to item 14, characterized in that the formulation contains 2 to 8% (by weight) of aluminium stearate, preferably 3 to 6%.
20. Pharmaceutical formulation according to at least one of items 13-19, characterized in that the formulation contains furthermore medium-chained triglycerides, mineral oil, cyclomethicone, or mixtures thereof.
21. Pharmaceutical formulation according to item 1 furthermore containing
   d) mineral oil.
22. Pharmaceutical formulation according to item 21, characterized in that the formulation contains 10 to 50% (by weight) of oleyl alcohol, preferably 10 to 40%.
23. Pharmaceutical formulation according to item 21, characterized in that the formulation contains 10 to 50% (by weight) of cetearyl octanoate, preferably 20 to 40%.
24. Pharmaceutical formulation according to item 21, characterized in that the formulation contains 10 to 50% (by weight) of vegetable oil, preferably 16 to 30%.
25. Pharmaceutical formulation according to item 21, characterized in that the formulation contains 2 to 15% (by weight) of mineral oil, preferably 4 to 15%.
26. Pharmaceutical formulation according to at least one of items 21-25, characterized in that the formulation furthermore contains medium-chained triglycerides, cyclomethicone, or mixtures thereof.
27. Pharmaceutical formulation according to item 1 furthermore containing
   d) propylene glycol,
   e) glycerol,
   f) a propellant.
28. Pharmaceutical formulation according to item 27, characterized in that the formulation contains 2 to 15% (by weight) of oleyl alcohol, preferably 3 to 10%.

29. Pharmaceutical formulation according to item 27, characterized in that the formulation contains 2 to 10% (by weight) of cetearyl octanoate, preferably 3 to 5%.

30. Pharmaceutical formulation according to item 27, characterized in that the formulation contains 2 to 10% (by weight) of vegetable oil, preferably 3 to 5%.

31. Pharmaceutical formulation according to item 27, characterized in that the formulation contains 2 to 10% (by weight) of glycerol (85%), preferably 4 to 8%.

32. Pharmaceutical formulation according to item 27, characterized in that the formulation contains 2 to 10% (by weight) of propylene glycol, preferably 4 to 10%.

33. Pharmaceutical formulation according to at least one of items 27-32, characterized in that the formulation contains 2 to 10% (by weight) of propellant, preferably 6 to 8%.

34. Pharmaceutical formulation according to item 33, characterized in that the propellants are hydrocarbons such as propane, butane, isobutane or a mixture of these; a hydrofluoroalkane such as heptafluoropropane or tetrafluoroethane, dimethylether, or mixtures thereof.

35. Pharmaceutical formulation according to at least one of items 27-34, characterized in that the formulation contains furthermore macrogolglycerolhydroxystearate, macrogol-400-stearate, methylcellulose, xanthan gum, parts of these or mixtures thereof.

36. Pharmaceutical formulation according to any of items 1-35 characterized in that the solubility of at least one pharmaceutically active compound in water is 20 mg/l at 20° C. or less.

37. Pharmaceutical formulation according to item 36 characterized in that the solubility of at least one pharmaceutically active compound in water is 2 mg/l at 20° C. or less.

Pharmaceutical formulation according to any of items 1-37 characterized in that the pharmaceutically active compound includes glucocorticosteroids, steroids, calcineurin inhibitors, vitamin D analogues, retinoids, immunosuppressants, antimycotics, antiinfectives, estrogens, androgens, fumaric acid esters
or
a glucocorticoid including but not limited to betametasone, clobetasol, dexametasone, prednicarbate, clocortolone, mometasone, methylprednisolone, esters and salts thereof
or
an antimycotic drug substance, including but not limited to bifonazole, clotrimazole, itraconazole, fluconazole, terbinafine
or
a vitamin D analogue including but not limited to Calcipotriol, Calcitriol, Tacalcitol, or (R)-1,1,1-Trifluoro-4-(5-fluoro-2,3-dihydrobenzofuran-7-yl)-4-methyl-2-{[(2-methyl-5-quinolyl)amino]methyl}pentan-2-ol or other compounds disclosed in WO 2006/050998 or WO 03/082827, which correspond to U.S. Pat. No. 7,417,056 and U.S. Pat. No. 7,329,753, respectively, the disclosures of which are incorporated by reference herein, which include compounds of formulae (IIA) and (IIb) for WO 2006/050998, (IIa)

(IIb)

in which
$R^1$ and $R^2$ are, independently of one another, a hydrogen atom, a $C_{1-3}$-alkyl group, a halogen atom, a cyano group, a $C_{1-3}$-alkoxy group or a hydroxy group,
or a pharmaceutically acceptable salt thereof,
and compounds of formula (I) for WO 03/082827, (I)

in which
A stands for an aryl group, a benzyl group or a phenethyl group, wherein the aryl, benzyl or phenethyl group is optionally substituted by one or more $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, —O—$(CH_2)_n$—O—, —O—$(CH_2)_n$—$CH_2$—, —O—CH=CH—, or —$(CH)_{n+2}$—, wherein n=1 or 2, and the terminal oxygen atoms and/or carbon atoms are linked with directly adjacent ring-carbon atoms, or $NR^4R^5$,
$R^1$ and $R^2$ are, independently of one another, a hydrogen atom, a methyl or ethyl group or together with the carbon atom the chain of a $C_3$-$C_6$-cycloalkyl ring,
$R^3$ means a $C_1$-$C_1$-alkyl group or a $C_1$-$C_3$-alkyl group that is optionally partially or completely fluorinated,
B means a methylene group that is optionally substituted by a methyl or ethyl group, or a carbonyl group,
Q means a quinolinyl group or isoquinolinyl group that is linked via any position and that is optionally substituted by one or more $C_1$-$C_5$-alkyl, which is optionally substituted by 1-3 hydroxy groups and/or 1-3 $COOR^6$ groups, $C_1$-$C_5$-alkoxy, $C_1$-$C_5$-alkylthio, $C_1$-$C_5$-perfluoroalkyl, halogen, hydroxy, a carbonyl-oxygen atom, cyano, nitro, $NR^4R^5$, $COOR^6$, $(CO)NR^7R^8$, or a $(C_1$-$C_5$-alkylene)-O—(CO)—$(C_1$-$C_5)$alkyl group,
$R^4$ and $R^5$ are, independently of one another, hydrogen, $C_1$-$C_5$-alkyl or (CO)—$C_1$-$C_5$-alkyl,
$R^6$ means hydrogen or a $C_1$-$C_5$-alkyl group,
$R^7$ and $R^8$ are, independently of one another, hydrogen or a $C_1$-$C_5$-alkyl group,
or a pharmaceutically acceptable salt thereof,
or
a corticosteroid, such as prednisone or fludrocortisone,
or
a calcineurin inhibitor, such as tacrolimus or pimecrolimus.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 07013369.9, filed Jul. 9, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLES

The present invention is further described in the following examples, which shall not be interpreted as limiting in any way.

| Examples (cream) | 1 | 2 | 3 | 4 | 5 | Ranges |
|---|---|---|---|---|---|---|
| active compound | 0.10 | 0.10 | 0.10 | 0.10 | 0.10 | 0.001-0.50 |
| Oleyl alcohol | 10.00 | 10.00 | 10.00 | 5.00 | 10.00 | 3.00-15.00 |
| Medium-chained triglycerides | — | — | — | 5.00 | — | 2.00-10.00 |
| Mineral oil | 8.00 | 4.00 | 4.00 | 4.00 | 4.00 | 2.00-10.00 |
| Cetearyl octanoate | 3.00 | 10.00 | 10.00 | 10.00 | 10.00 | 2.00-15.00 |
| Soybean Oil (vegetable oils) | 6.00 | 4.00 | 4.00 | 4.00 | 4.00 | 3.00-15.00 |
| Cyclomethicone | 3.50 | 2.50 | 2.50 | 2.50 | 2.50 | 1.00-5.00 |
| Stearyl alcohol | 2.00 | 2.00 | 2.00 | 2.00 | 2.00 | 1.00-5.00 |
| Butylated hydroxytoluene | 0.05 | 0.05 | 0.05 | 0.05 | 0.05 | 0.01-0.20 |
| Glycerol (85%) | 8.00 | 8.00 | 8.00 | 8.00 | 8.00 | 4.00-10.00 |
| Macrogolglycerolhydroxystearate | 1.50 | 1.50 | 1.50 | 1.50 | 1.50 | 0.50-5.00 |
| Povidone 90 | 4.00 | 4.00 | 4.00 | 4.00 | 4.00 | 2.00-8.00 |
| Propylene Glycol | 8.00 | 8.00 | 8.00 | 8.00 | 8.00 | 4.00-10.00 |
| Acrylic acid copolymer | 0.30 | — | 0.30 | 0.30 | — | 0.10-1.00 |
| Hydroxyethylcellulose | — | 1.50 | — | — | — | 0.10-1.00 |
| Acrylic acid | — | — | — | — | 1.00 | 0.50-2.00 |
| Trometamol solution 10% | to pH 7 | to pH 7 | to pH 7 | to pH 7 | to pH 7 | to pH 7.0 |
| Purified water | [ad 100.0] | [ad 100.0] | [ad 100.0] | [ad 100.0] | [ad 100.0] | [ad 100.0] |

| Examples (liquid spray) | 1 | 2 | 3 | 4 | 5 | Ranges |
|---|---|---|---|---|---|---|
| active compound | 0.10 | 0.10 | 0.10 | 0.10 | 0.10 | 0.001-0.5 |
| Oleyl alcohol | 40.00 | 30.00 | 20.00 | 35.00 | 10.00 | 10.00-50.00 |
| Medium-chained triglycerides | — | 10.00 | — | 5.00 | 10.00 | 2.00-15.00 |
| Mineral oil | — | 4.00 | 10.00 | 4.00 | 15.00 | 2.00-15.00 |
| Cetearyl octanoate | 40.00 | 30.00 | 40.00 | 35.00 | 20.00 | 10.00-50.00 |
| Soybean Oil (vegetable oils) | 19.90 | 20.00 | 20.00 | 16.00 | 30.00 | 10.00-50.00 |
| Cyclomethicone | — | 5.90 | 9.90 | 4.90 | 14.90 | 1.00-15.00 |

| Examples (foam) | 1 | 2 | 3 | 4 | 5 | Ranges |
|---|---|---|---|---|---|---|
| active compound | 0.10 | 0.10 | 0.10 | 0.10 | 0.10 | 0.001-0.50 |
| Oleyl alcohol | 10.00 | 5.00 | 3.00 | 10.00 | 4.00 | 2.00-15.00 |
| Medium-chained triglycerides | — | 5.00 | 10.0 | — | 6.00 | 2.00-15.00 |
| Mineral oil | 4.00 | — | — | — | — | 2.00-6.00 |
| Cetearyl octanoate | 3.00 | 5.00 | 3.00 | 5.00 | 4.00 | 2.00-10.00 |
| Soybean Oil (vegetable oils) | 3.00 | 5.00 | 2.00 | — | 5.00 | 2.00-10.00 |
| Stearyl alcohol | 2.00 | — | — | — | 1.00 | 0.50-5.00 |
| Cetostearyl alcohol | — | 1.50 | 1.50 | 1.50 | 1.00 | 0.50-5.00 |
| Glyceryl Stearate | — | 0.50 | 0.50 | 0.50 | 0.50 | 0.50-2.00 |
| Glycerol (85%) | 8.00 | — | 4.00 | 8.00 | — | 2.00-10.00 |
| Macrogolglycerolhydroxystearate | 1.50 | — | — | — | 1.50 | 0.50-5.00 |
| Macrogol-400-Stearate | — | 2.50 | 2.00 | 2.50 | 1.00 | 0.50-5.00 |
| Polysorbate 80 | — | 1.00 | 1.50 | 1.00 | 1.00 | 0.50-3.00 |
| Povidone 90 | 2.00 | — | — | — | — | 0.00-3.00 |
| Propylene Glycol | 8.00 | 8.00 | 8.00 | 10.00 | 4.00 | 2.00-10.00 |
| Methylcellulose | 0.10 | 0.10 | 0.10 | 0.15 | 0.10 | 0.05-1.00 |
| Xanthan gum | 0.30 | 0.20 | 0.10 | 0.20 | 0.30 | 0.05-2.00 |

-continued

| Examples (foam) | 1 | 2 | 3 | 4 | 5 | Ranges |
|---|---|---|---|---|---|---|
| Trometamol 10% | to pH 7 | to pH 7 | to pH 7 | to pH 7 | to pH 7 | to pH 7.0 |
| Purified water | [ad 100.0] | [ad 100.0] | [ad 100.0] | [ad 100.0] | [ad 100.0] | [ad 100.0] |
| Propellant | | | 2.0-10.0 for all examples | | | |

| Examples (oleogel) | 1 | 2 | 3 | 4 | 5 | Ranges |
|---|---|---|---|---|---|---|
| active compound | 0.10 | 0.10 | 0.10 | 0.10 | 0.10 | 0.001-0.5 |
| Oleyl alcohol | 30.00 | 20.00 | 20.00 | 15.00 | 15.00 | 10.00-40.00 |
| Medium-chained triglycerides | — | 20.00 | 20.00 | 15.00 | 20.00 | 10.00-30.00 |
| Mineral oil | 5.00 | 20.00 | 10.00 | 20.00 | 20.00 | 2.00-25.00 |
| Cetearyl octanoate | 30.00 | 10.00 | 20.00 | 20.00 | 20.00 | 5.00-40.00 |
| Soybean Oil (vegetable oils) | 20.00 | 20.00 | 20.00 | 20.00 | 15.00 | 10.00-30.00 |
| Cyclomethicone | — | 5.90 | 4.90 | 6.90 | 3.90 | 1.00-10.00 |
| Silicon dioxide | 5.00 | 4.00 | 5.00 | — | — | 3.00-10.00 |
| Aluminium stearate | — | — | — | 3.00 | 6.00 | 2.00-8.00 |

Example

Figure 1:
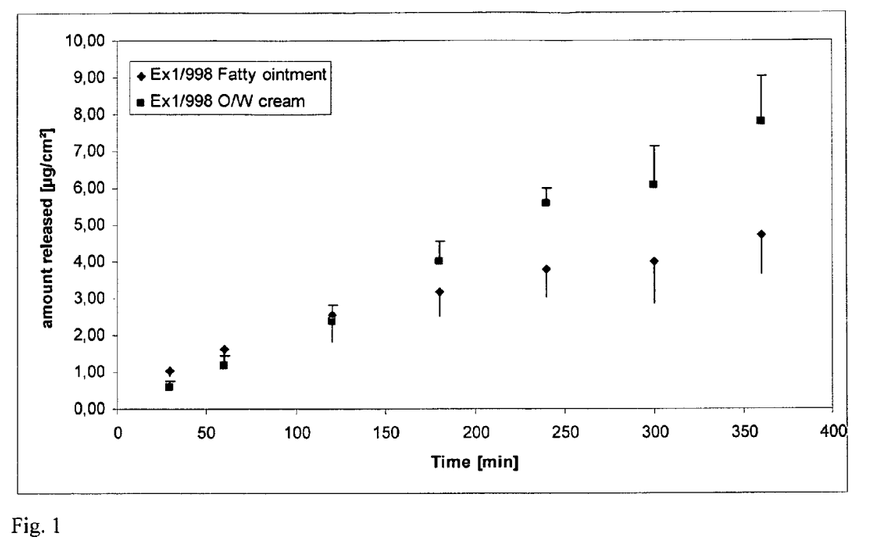
Figure 2:
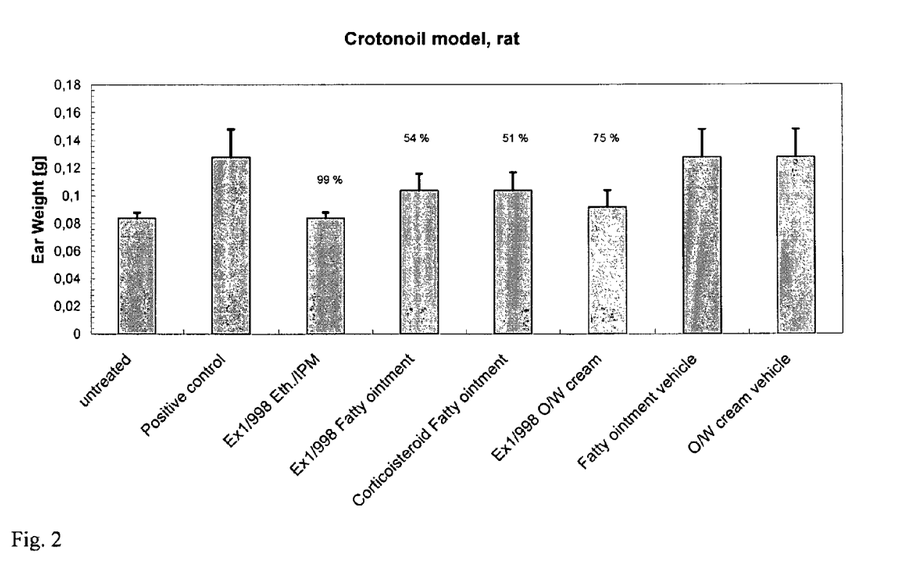

In-vitro release (see FIG. 1 as a proof that, surprisingly, the non-occlusive O/W cream is superior to the very occlusive fatty ointment formulation) using (R)-1,1,1-Trifluoro-4-(5-fluoro-2,3-dihydrobenzofuran-7-yl)-4-methyl-2-{[(2-methyl-5-quinolyl)amino]methyl}pentan-2-ol, (Ex1/998) as the poorly soluble compound Example In-vivo efficacy (see FIG. 2 to support in-vitro release data-values given in the figure represent percent reduction to ear weight relative to untreated)

(R)-1,1,1-Trifluoro-4-(5-fluoro-2,3-dihydrobenzofuran-7-yl)-4-methyl-2-{[(2-methyl-5-quinolyl)amino]methyl}pentan-2-ol (Ex1/998) in comparison to other anti-inflammatory compounds

The invention claimed is:

1. A pharmaceutical formulation containing at least one pharmaceutically active compound, which is

(R)-1,1,1-Trifluoro-4-(5-fluoro-2,3-dihydrobenzofuran-7-yl)-4-methyl-2-{[(2-methyl-5-quinolyl)amino]methyl}pentan-2-ol, or a compound of formula (IIa) or (IIb)

(IIa)

(IIb)

in which $R^1$ and $R^2$ are, independently of one another, a hydrogen atom, a $C_{1-3}$-alkyl group, a halogen atom, a cyano group, a $C_{1-3}$-alkoxy group or a hydroxy group, or a compound of formula (I)

(I)

in which

A stands for an aryl group, a benzyl group or a phenethyl group, wherein the aryl, benzyl or phenethyl group is optionally substituted by one or more $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, —O—$(CH_2)_n$—O—, —O—$(CH_2)_n$—$CH_2$—, —O—CH=CH—, or —$(CH_2)_{n+2}$—, wherein n=1 or 2, and the terminal oxygen atoms and/or carbon atoms are linked with directly adjacent ring-carbon atoms, or $NR^4R^5$, $R^1$ and $R^2$ are, independently of one another, a hydrogen atom, a methyl or ethyl group or together with the carbon atom the chain of a $C_3$-$C_6$-cycloalkyl ring, $R^3$ means a $C_1$-$C_3$-alkyl group or a $C_1$-$C_3$-alkyl group that is optionally partially or completely fluorinated, B means a methylene group that is optionally substituted by a methyl or ethyl group, or a carbonyl group, Q means a quinolinyl group or isoquinolinyl group that is optionally substituted by one or more $C_1$-$C_5$-alkyl, which is optionally substituted by 1-3 hydroxy groups and/or 1-3 $COOR^6$ groups, $C_1$-$C_5$-alkoxy, $C_1$-$C_5$-alkylthio, $C_1$-$C_5$-perfluoroalkyl, halogen, hydroxy, a carbonyl-oxygen atom, cyano, nitro, $NR^4R^5$, $COOR^6$, (CO)$NR^7R^8$, or a ($C_1$-$C_5$-alkylene)—O—(CO)—($C_1$-$C_5$) alkyl group, $R^4$ and $R^5$ are, independently of one another, hydrogen, $C_1$-$C_5$-alkyl or (CO)—$C_1$-$C_5$-alkyl, $R^6$ means hydrogen or a $C_1$-$C_5$-alkyl group, $R^7$ and $R^8$ are, independently of one another, hydrogen or a $C_1$-$C_5$-alkyl group, or a pharmaceutically acceptable salt thereof, and a) 2 to 50% by weight of oleyl alcohol, b) 2 to 50% by weight of cetearyl octanoate and c) 2 to 50% by weight of a vegetable oil.

2. A pharmaceutical formulation according to claim 1, wherein the vegetable oil is soybean oil, olive oil, sesame oil, castor oil or peanut oil.

3. A pharmaceutical formulation according to claim 1, further containing
   d) propylene glycol and
   e) glycerol.

4. A pharmaceutical formulation according to claim 3, which contains 3 to 15% (by weight) of oleyl alcohol.

5. A pharmaceutical formulation according to claim 3, which contains 2 to 15% (by weight) of cetearyl octanoate.

6. A pharmaceutical formulation according to claim 3, which contains 3 to 15% (by weight) of vegetable oil.

7. A pharmaceutical formulation according to claim 3, which further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol.

8. A pharmaceutical formulation according to claim 1, further containing
   d) silicon dioxide.

9. A pharmaceutical formulation according to claim 1, further containing
   d) aluminium stearate.

10. A pharmaceutical formulation according to claim 1, further containing
    d) propylene glycol,
    e) glycerol, and
    f) propellant.

11. A pharmaceutical formulation according to claim 10, which contains 2 to 10% (by weight) of propellant.

12. A pharmaceutical formulation according to claim 11, wherein the propellant is a hydrocarbon or hydrofluoroalkane.

13. A pharmaceutical formulation according to claim 1, wherein the solubility of at least one pharmaceutically active compound in water is 20 mg/l at 20° C. or less.

14. A pharmaceutical formulation according to claim 1, which contains
    2 to 50% (by weight) of oleyl alcohol,
    3 to 20% (by weight) of cetearyl octanoate, and
    5 to 20% (by weight) of vegetable oil.

15. A pharmaceutical formulation according to claim 3, which contains
    3 to 15% (by weight) of oleyl alcohol,
    2 to 15% (by weight) of cetearyl octanoate,
    3 to 15% (by weight) of vegetable oil.

16. A pharmaceutical formulation according to claim 15, which further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol.

17. A pharmaceutical formulation according to claim 1, further containing silicon dioxide and aluminium stearate.

18. A pharmaceutical formulation according to claim 10, which contains 6 to 8% (by weight) of propellant.

19. A pharmaceutical formulation according to claim 11, wherein the propellant is propane, butane, isobutene, heptafluoropropane, tetrafluoroethane, dimethylether, or a mixture thereof.

20. A pharmaceutical formulation according to claim 11, which contains 6 to 8% (by weight) of propellant and wherein the propellant is propane, butane, isobutene, heptafluoropropane, tetrafluoroethane, dimethylether, or a mixture thereof.

21. A pharmaceutical formulation containing at least one pharmaceutically active compound, which is
    (R)-1,1,1-Trifluoro-4-(5-fluoro-2,3-dihydrobenzofuran-7-yl)-4-methyl-2-{[(2-methyl-5-quinolyl)amino]methyl} pentan-2-ol,
    5-[4-(5-Fluoro-2,3-dihydrobenzofuran-7-yl)-2-hydroxy-4-methyl-2-trifluoromethyl-pentylamino]-2-methylquinoline,
    5-[4-(5-Fluoro-2,3-dihydrobenzofuran-7-yl)-2-hydroxy-4-methyl-2-trifluoromethyl-pentylamino]-1-methylisoquinoline),
    5-[4-(5-Fluoro-2,3-dihydrobenzofuran-7-yl)-2-hydroxy-4-methyl-2-trifluoromethyl-pentylamino]isoquinol-1(2H)-one,
    5-[4-(5-Fluoro-2,3-dihydrobenzofuran-7-yl)-2-hydroxy-4-methyl-2-trifluoromethyl-pentylamino]-2,6-dimethylquinoline,
    5-[4-(5-Fluoro-2,3-dihydrobenzofuran-7-yl)-2-hydroxy-4-methyl-2-trifluoromethyl-pentylamino]-6-chloro-2-methylquinoline,
    5-[4-(5-Fluoro-2,3-dihydrobenzofuran-7-yl)-2-hydroxy-4-methyl-2-trifluoromethyl-pentylamino] isoquinoline,
    5-[4-(5-Fluoro-2,3-dihydrobenzofuran-7-yl)-2-hydroxy-4-methyl-2-trifluoromethyl-pentylamino]quinoline,
    5-[4-(2,3-Dihydro-5-fluoro-7-benzofuranyl)-2-hydroxy-4-methyl-2-trifluoromethyl-pentylamino]quinolin-2[1H]-one,
    6-Fluoro-5-[4-(5-fluoro-2,3-dihydrobenzofuran-7-yl)-2-hydroxy-4-methyl-2-trifluoromethyl-pentylamino]-2-methylquinoline,
    8-Fluoro-5-[4-(5-fluoro-2,3-dihydrobenzofuran-7-yl)-2-hydroxy-4-methyl-2-trifluoromethyl-pentylamino]-2-methylquinoline,
    5-[4-(5-Fluoro-2,3-dihydrobenzofuran-7-yl)-2-hydroxy-4-methyl-2-trifluoromethyl-pentylamino]-2-methylisoquinol-1(2H)-one, as well as their separate enantiomers:
    2(R)-5-[4-(5-Fluoro-2,3-dihydrobenzofuran-7-yl)-2-hydroxy-4-methyl-2-trifluoromethyl-pentylamino]-2-methylquinoline),
    2(R)-5-[4-(5-fluoro-2,3-dihydrobenzofuran-7-yl)-2-hydroxy-4-methyl-2-trifluoromethyl-pentylamino]-1-methylisoquinoline,
    2(R)-5-[4-(5-Fluoro-2,3-dihydrobenzofuran-7-yl)-2-hydroxy-4-methyl-2-trifluoromethyl-pentylamino]isoquinol-1(2H)-one,
    2(R)-5-[4-(5-Fluoro-2,3-dihydrobenzofuran-7-yl)-2-hydroxy-4-methyl-2-trifluoromethyl-pentylamino]-2,6-dimethylquinoline,
    2(R)-5-[4-(5-Fluoro-2,3-dihydrobenzofuran-7-yl)-2-hydroxy-4-methyl-2-trifluoromethyl-pentylamino]-6-chloro-2-methylquinoline,
    2(R)-5-[4-(5-Fluoro-2,3-dihydrobenzofuran-7-yl)-2-hydroxy-4-methyl-2-trifluoromethyl-pentylamino]isoquinoline,
    2(R)-5-[4-(5-Fluoro-2,3-dihydrobenzofuran-7-yl)-2-hydroxy-4-methyl-2-trifluoromethyl-pentylamino]quinoline,
    2(R)-5-[4-(2,3-Dihydro-5-fluoro-7-benzofuranyl)-2-hydroxy-4-methyl-2-trifluoromethyl-pentylamino]quinolin-2[1H]-one,
    2(R)-6-Fluoro-5-[4-(5-fluoro-2,3-dihydrobenzofuran-7-yl)-2-hydroxy-4-methyl-2-trifluoromethyl-pentylamino]-2-methylquinoline,
    2(R)-8-Fluoro-5-[4-(5-fluoro-2,3-dihydrobenzofuran-7-yl)-2-hydroxy-4-methyl-2-trifluoromethyl-pentylamino]-2-methylquinoline, 2(R)-5-[4-(5-Fluoro-2,3-dihydrobenzofuran-7-yl)-2-hydroxy-4-methyl-2-trifluoromethyl-pentylamino]-2-methylquinol-1(2H)-one,
2(S)-5-[4-(5-Fluoro-2,3-dihydrobenzofuran-7-yl)-2-hydroxy-4-methyl-2-trifluoromethyl-pentylamino]-2-methylquinoline),
2(S)-5-[4-(5-Fluoro-2,3-dihydrobenzofuran-7-yl)-2-hydroxy-4-methyl-2-trifluoromethyl-pentylamino]-1-methylisoquinoline),
2(S)-5-[4-(5-Fluoro-2,3-dihydrobenzofuran-7-yl)-2-hydroxy-4-methyl-2-trifluoromethyl-pentylamino]isoquinol-1(2H)-one,
2(S)-5-[4-(5-Fluoro-2,3-dihydrobenzofuran-7-yl)-2-hydroxy-4-methyl-2-trifluoromethyl-pentylamino]-2,6-dimethylquinoline,
2(S)-5-[4-(5-Fluoro-2,3-dihydrobenzofuran-7-yl)-2-hydroxy-4-methyl-2-trifluoromethyl-pentylamino]-6-chloro-2-methylquinoline,
2(S)-5-[4-(5-Fluoro-2,3-dihydrobenzofuran-7-yl)-2-hydroxy-4-methyl-2-trifluoromethyl-pentylamino]isoquinoline,
2(S)-5-[4-(5-Fluoro-2,3-dihydrobenzofuran-7-yl)-2-hydroxy-4-methyl-2-trifluoromethyl-pentylamino]quinoline,
2(S)-5-[4-(2,3-Dihydro-5-fluoro-7-benzofuranyl)-2-hydroxy-4-methyl-2-trifluoromethyl-pentylamino]quinolin-2[1H]-one,
2(S)-6-Fluoro-5-[4-(5-fluoro-2,3-dihydrobenzofuran-7-yl)-2-hydroxy-4-methyl-2-trifluoromethyl-pentylamino]-2-methylquinoline,
2(S)-8-Fluoro-5-[4-(5-fluoro-2,3-dihydrobenzofuran-7-yl)-2-hydroxy-4-methyl-2-trifluoromethyl-pentylamino]-2-methylquinoline,
2(S)-5-[4-(5-Fluoro-2,3-dihydrobenzofuran-7-yl)-2-hydroxy-4-methyl-2-trifluoromethyl-pentylamino]-2-methylisoquinol-1(2H)-one
1-(Quinolin-8-ylamino)-4-(5-fluoro-2-methoxyphenyl)-4-methyl-2-(trifluorom-ethyl)pentan-2-ol
1-(Quinolin-8-ylamino)-4-(5-fluoro-2-hydroxyphenyl)-4-methyl-2-(trifluorom-ethyl)pentan-2-ol
1-(Quinolin-5-ylamino)-4-(5-fluoro-2-methoxyphenyl)-4-methyl-2-(trifluorom-ethyl)pentan-2-ol
1-(Quinolin-5-ylamino)-4-(5-fluoro-2-methoxyphenyl)-4-methyl-2-(trifluorom-ethyl)pentan-2-ol
1-(Quinolin-4-ylamino)-4-(5-fluoro-2-methoxyphenyl)-4-methyl-2-(trifluorom-ethyl)pentan-2-ol
1-(Quinolin-4-ylamino)-4-(5-fluoro-2-hydroxyphenyl)-4-methyl-2-(trifluorom-ethyl)pentan-2-ol
4-(5-Fluoro-2-methoxyphenyl)-1-(isoquinolin-1-ylamino)-4-methyl-2-(trifluo-romethyl)pentan-2-ol
4-(5-Fluoro-2-hydroxyphenyl)-1-(isoquinolin-1-ylamino)-4-methyl-2-(trifluo-romethyl)pentan-2-ol
1-(Quinolin-5-ylamino)-4-methyl-4-phenyl-2-(trifluoromethyl)pentan-2-ol
1-(Quinolin-5-ylamino)-4-methyl-4-phenyl-2-(trifluoromethyl)pentan-2-ol
4-Methyl-1-(2-methylquinolin-5-ylamino)-4-phenyl-2-(trifluoromethyl)pentan-2-ol
N-(Quinolin-5-yl)-4-(5-fluoro-2-methoxyphenyl)-2-hydroxy-4-methyl-2-(trifluoromethyl)pentanoic Acid Amide
4-(1,3-Benzodioxol-4-yl)-N-(quinolin-5-yl)-2-hydroxy-4-methyl-2-(trifluoromethyl)pentanamide
N-(Quinolin-5-yl)-4-(2-chlorophenyl)-2-hydroxy-4-methyl-2-(trifluoromethyl-)-pentanamide
N-(Quinolin-5-yl)-4-(2-chloro-5-fluorophenyl)-2-hydroxy-4-methyl-2-(trifluoromethyl)pentanamide
N-(Quinolin-5-yl)-3-[1-(2-chloro-4-fluorophenyl)-cyclopropyl]-2-hydroxy-2-(trifluoromethyl)propanamide
4-(4-Bromo-2-methoxyphenyl)-1-(quinolin-5-ylamino)-2-hydroxy-4-methyl-2-(trifluoromethyl)pentan-2-ol
4-(5-Bromo-2-methoxyphenyl)-N-(quinolin-5-yl)-2-hydroxy-4-methyl-2-(trifluoromethyl)pentanamide
4-(4-Bromo-2-methoxyphenyl)-N-(quinolin-5-yl)-2-hydroxy-4-methyl-2-(trifluoromethyl)pentanamide
N-(Quinolin-5-yl)-)-2-hydroxy-4-methyl-4-phenyl-2-(trifluoromethyl)pentanamide
4-(5-Fluoro-2-methoxyphenyl)-1-(2-methoxyquinolin-5-ylamino)-4-methyl-2-(trifluoromethyl)pentan-2-ol
4-(5-Fluoro-2-hydroxyphenyl)-1-(2-methoxyquinolin-5-ylamino)-4-methyl-2-(trifluoromethyl)pentan-2-ol
1-(2-Ethoxyquinolin-5-ylamino)-4-(5-fluoro-2-methoxyphenyl)-4-methyl-2-(trifluoromethyl)pentan-2-ol
4-(5-Fluoro-2-methoxyphenyl)-1-(2-hydroxyquinolin-5-ylamino)-4-methyl-2-(trifluoromethyl)pentan-2-ol
4-(5-Fluoro-2-methoxyphenyl)-1-(2-quinolon-5-ylamino)-4-methyl-2-(trifluoromethyl)pentan-2-ol
1-(2-Acetylaminoquinolin-5-ylamino)-4-(5-fluoro-2-hydroxyphenyl)-4-methyl-2-(trifluoromethyl)pentan-2-ol
4-(5-Fluoro-2-hydroxyphenyl)-4-methyl-1-(2-(methylamino)quinolin-5-ylamino-)-2-(trifluoromethyl)pentan-2-ol
4-(5-Fluoro-2-methoxyphenyl)-4-methyl-1-(2-methylquinolin-5-ylamino)-2-(trifluoromethyl)pentan-2-ol
4-(5-Fluoro-2-hydroxyphenyl)-4-methyl-1-(2-methylquinolin-5-ylamino)-2-(trifluoromethyl)-pentan-2-ol
5-[4-(5-Fluoro-2-methoxyphenyl)-2-hydroxy-4-methyl-2-trifluoromethylpentyl-amino]quinoline-2-carboxylic Acid Amide
5-[4-(5-Fluoro-2-methoxyphenyl)-2-hydroxy-4-methyl-2-trifluoromethylpentyl-amino]quinoline-2-carboxylic Acid Amide
5-[4-(5-Fluoro-2-hydroxyphenyl]-2-hydroxy-4-methyl-2-trifluoromethylpentyl-amino]quinoline-2-carboxylic Acid Amide
4-(5-Fluoro-2-methoxyphenyl)-4-methyl-2-trifluorom-ethyl-1-(2-(trifluoromethyl)quinolin-5-ylamino)pentan-2-ol
4-(5-Fluoro-2-hydroxyphenyl)-4-methyl-2-trifluorom-ethyl-1-(2-(trifluoromethyl)-quinolin-5-ylamino)pentan-2-ol
1-(2-(Acetoxymethyl)quinolin-5-ylamino)-4-(5-fluoro-2-methoxyphenyl)-4-methyl-2-(trifluoromethyl)pentan-2-ol
4-(5-Fluoro-2-methoxyphenyl)-1-(2-(hydroxymethyl)quinolin-5-ylamino)-4-methyl-2-(trifluoromethyl)pentan-2-ol
4-(5-Fluoro-2-hydroxyphenyl)-1-(2-(hydroxymethyl)quinolin-5-ylamino)-4-methyl-2-(trifluoromethyl)pentan-2-ol
5-[4-(5-Fluoro-2-hydroxyphenyl)-2-hydroxy-4-methyl-2-(trifluoromethyl)pentylamino]-quinoline-2-carboxylic Acid Methylamide
3-[1-(5-Fluoro-2-hydroxyphenyl)cycloprop-1-yl]-1-(2-(hydroxymethyl)quinolin-5-ylamino)-2-(trifluoromethyl)propan-2-ol or
5-[(4-(5-Fluoro-2-methoxyphenyl)-2-hydroxy-4-methyl-2-(trifluoromethyl)pentylamino]quinoline-2-carboxylic Acid Diethylamide
or
a pharmaceutically acceptable salt thereof,
and
a) 2 to 50% by weight of oleyl alcohol,
b) 2 to 50% by weight of cetearyl octanoate and
c) 2 to 50% by weight of a vegetable oil.

22. A pharmaceutical formulation according to claim 21, further containing
d) propylene glycol and
e) glycerol.

23. A pharmaceutical formulation according to claim 22, which contains 3 to 15% (by weight) of oleyl alcohol,
2 to 15% (by weight) of cetearyl octanoate,
3 to 15% (by weight) of vegetable oil.

24. A pharmaceutical formulation according to claim 21, which further contains a medium-chained triglyceride, mineral oil, cyclomethicone, stearyl alcohol, butylated hydroxytoluene, macrogolglycerolhydroxystearate, povidone, acrylic acid copolymer, hydroxyethylcellulose, acrylic acid, and/or trometamol.

25. A pharmaceutical formulation according to claim 21, further containing silicon dioxide or aluminium stearate.

26. A pharmaceutical formulation according to claim 21, further containing
d) propylene glycol,
e) glycerol, and
f) a propellant.

27. A pharmaceutical formulation according to claim 26, which contains 2 to 10% (by weight) of propellant.

28. A pharmaceutical formulation according to claim 27, wherein the propellant is a hydrocarbon or a hydrofluoroalkane.

29. A pharmaceutical formulation according to claim 28, wherein the propellant is propane, butane, isobutene, heptafluoropropane, tetrafluoroethane, dimethylether, or a mixture thereof.

30. A pharmaceutical formulation according to claim 27, which contains 6 to 8% (by weight) of propellant and wherein the propellant is propane, butane, isobutene, heptafluoropropane, tetrafluoroethane, dimethylether, or a mixture thereof.

31. A pharmaceutical formulation according to claim 21, wherein the solubility of at least one pharmaceutically active compound in water is 20 mg/l at 20° C. or less.

32. A pharmaceutical formulation according to claim 21, which contains (R)-1,1,1-Trifluoro-4-(5-fluoro-2,3-dihydrobenzofuran-7-yl)-4-methyl-2-{[(2-methyl-5-quinolyl)amino]methyl}pentan-2-ol.

33. A pharmaceutical formulation according to claim 21, which contains
2 to 50% (by weight) of oleyl alcohol,
3 to 20% (by weight) of cetearyl octanoate, and
5 to 20% (by weight) of vegetable oil.

* * * * *